(12) United States Patent　(10) Patent No.: US 10,102,643 B2
Sato　(45) Date of Patent: Oct. 16, 2018

(54) ENDOSCOPE APPARATUS AND INSPECTION METHOD USING ENDOSCOPE

(71) Applicant: OLYMPUS CORPORATION, Tokyo (JP)

(72) Inventor: Saichi Sato, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 59 days.

(21) Appl. No.: 15/098,661

(22) Filed: Apr. 14, 2016

(65) Prior Publication Data

US 2016/0225168 A1　Aug. 4, 2016

Related U.S. Application Data

(63) Continuation of application No. PCT/JP2014/068417, filed on Jul. 10, 2014.

(30) Foreign Application Priority Data

Oct. 17, 2013　(JP) ................. 2013-216716

(51) Int. Cl.
*G06T 7/60*　(2017.01)
*G06T 11/00*　(2006.01)
(Continued)

(52) U.S. Cl.
CPC ............ *G06T 7/60* (2013.01); *G02B 23/2484* (2013.01); *G06T 3/20* (2013.01); *G06T 5/50* (2013.01);
(Continued)

(58) Field of Classification Search
None
See application file for complete search history.

(56) References Cited

U.S. PATENT DOCUMENTS 5,877,819 A * 3/1999 Branson ............... G06F 19/321
348/620
2007/0003016 A1* 1/2007 Brunner ................ A61B 6/466
378/98.12
(Continued)

FOREIGN PATENT DOCUMENTS

CN　　103347436 A　10/2013
EP　　2664272 A1　11/2013
(Continued)

OTHER PUBLICATIONS

Ieiri, Satoshi, et al. "Augmented reality navigation system for laparoscopic splenectomy in children based on preoperative CT image using optical tracking device." Pediatric surgery international 28.4 (2012): 341-346.*

(Continued)

*Primary Examiner* — Maurice L McDowell, Jr.
*Assistant Examiner* — Donna J Ricks
(74) *Attorney, Agent, or Firm* — Scully, Scott, Murphy & Presser, P.C.

(57) ABSTRACT

An endoscope apparatus includes: a reference image generating section that generates a reference image to be used for determining whether an inspection object is non-defective or defective; and a mixer that outputs the reference image in a superimposed manner on an endoscopic image from an endoscope, the endoscopic image being obtained by photographing the inspection object, in a predetermined inspection mode, and an image of the inspection object and the reference image are displayed in a superimposed manner, to thereby facilitate a non-defective/defective determination and improve an operability in an inspection.

19 Claims, 7 Drawing Sheets

(51) Int. Cl.
*G06T 3/20* (2006.01)
*G06T 11/20* (2006.01)
*G06T 11/60* (2006.01)
*G06T 5/50* (2006.01)
*G06T 7/00* (2017.01)
*G02B 23/24* (2006.01)
*A61B 1/00* (2006.01)
*A61B 1/005* (2006.01)
*H04N 5/225* (2006.01)

(52) U.S. Cl.
CPC .............. *G06T 7/001* (2013.01); *G06T 11/00* (2013.01); *G06T 11/20* (2013.01); *G06T 11/60* (2013.01); *A61B 1/0005* (2013.01); *A61B 1/00009* (2013.01); *G06T 2207/10068* (2013.01); *G06T 2207/20221* (2013.01); *H04N 2005/2255* (2013.01)

(56) References Cited

U.S. PATENT DOCUMENTS

| | | | | |
|---|---|---|---|---|
| 2008/0304725 | A1* | 12/2008 | Leitner | A61B 1/317 382/128 |
| 2009/0088634 | A1* | 4/2009 | Zhao | B25J 9/1689 600/427 |
| 2010/0130836 | A1* | 5/2010 | Malchano | A61B 1/05 600/301 |
| 2012/0157773 | A1* | 6/2012 | Honda | A61B 1/00096 600/164 |
| 2012/0209123 | A1* | 8/2012 | King | A61B 1/0005 600/476 |
| 2013/0044126 | A1* | 2/2013 | Yamada | H04N 7/183 345/629 |
| 2013/0286174 | A1 | 10/2013 | Urakabe | |
| 2015/0054929 | A1* | 2/2015 | Ito | A61B 1/273 348/65 |
| 2015/0374210 | A1* | 12/2015 | Durr | A61B 1/041 600/111 |

FOREIGN PATENT DOCUMENTS

| | | |
|---|---|---|
| JP | 2008-061659 A | 3/2008 |
| JP | 2009-199089 A | 9/2009 |
| JP | 2012-123054 A | 6/2012 |
| JP | 2012-157683 A | 8/2012 |
| WO | WO 2012/096312 A1 | 7/2012 |

OTHER PUBLICATIONS

International Search Report dated Sep. 22, 2014 issued in PCT/JP2014/068417.

* cited by examiner

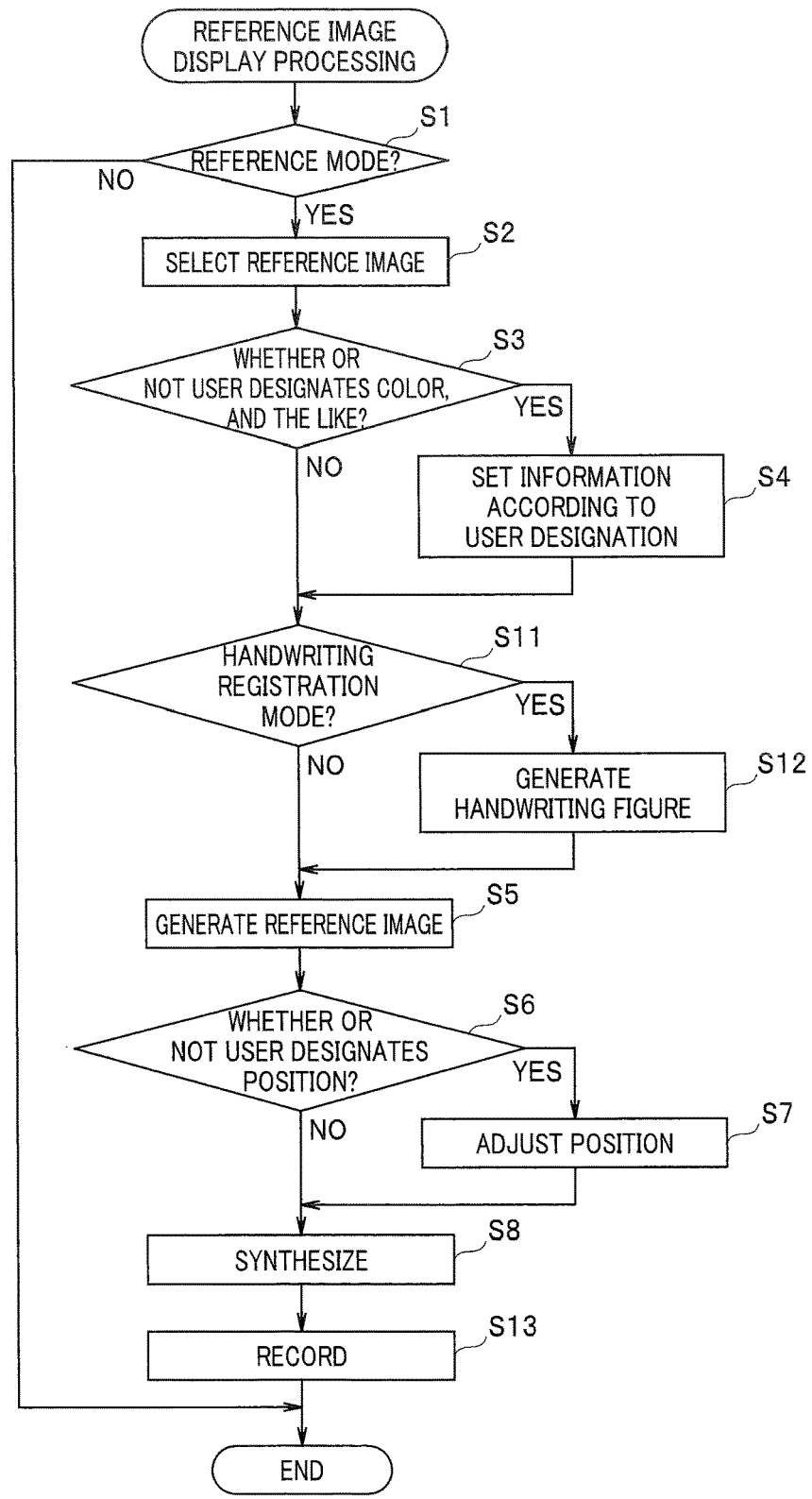

ENDOSCOPE APPARATUS AND INSPECTION METHOD USING ENDOSCOPE

CROSS REFERENCE TO RELATED APPLICATION

This application is a continuation application of PCT/JP2014/068417 filed on Jul. 10, 2014 and claims benefit of Japanese Application No. 2013-216716 filed in Japan on Oct. 17, 2013, the entire contents of which are incorporated herein by this reference.

BACKGROUND OF THE INVENTION

1. Field of the Invention

The present invention relates to an endoscope apparatus preferable for inspection and an inspection method using an endoscope.

2. Description of the Related Art

Conventionally, endoscopes have been widely used for performing observation or various kinds of treatment on a subject to be examined by inserting an elongated endoscope into a body cavity, and the like. Also in industrial fields, industrial endoscopes, which are capable of observing and inspecting flaws, corrosion, and the like in a boiler, turbine, engine, chemical plant, etc., have been widely used.

An endoscope includes an elongated insertion portion and is capable of observing an object image, which is imported from the distal end portion of the insertion portion, at the proximal end side of the insertion portion. An image pickup device such as CCD is provided at the distal end portion of the insertion portion, or a camera is attached to an eye piece portion on the proximal end side of the insertion portion, to thereby convert the object image into a video signal and enable the video signal to be transmitted to a processor connected to the operator's hand side position of the endoscope. The processor generates an endoscopic image based on the transmitted video signal, and sends the endoscopic image to the monitor to cause the monitor to display the endoscopic image.

Incidentally, a rigid endoscope is sometimes used for determining whether an inspection object is non-defective or defective. The distance between the inspection object and the distal end portion of the insertion portion of the rigid endoscope is fixed by inserting the rigid endoscope from an inspection hole using a jig. This allows the inspection object to be displayed in a certain definite size all the time on the display screen of the monitor, which enables a flaw size or the like to be confirmed easily.

However, it is sometimes difficult to determine whether the inspection object is non-defective or defective by just looking at the endoscopic image displayed on the display screen of the monitor. For example, when the non-defective or defective determination is made based on whether the size of the flaw is larger than a threshold, there is a case where the size of the flaw is close to the threshold. In such a case, it is not easy to determine whether the inspection object is non-defective or defective by just looking at the endoscopic image displayed on the display screen, and it is sometimes necessary to measure the dimension of the flaw.

In view of the above-described circumstances, Japanese Patent Application Laid-Open Publication No. 2009-199089 proposes an endoscope apparatus capable of performing stereoscopic measurement for measuring the dimension of such a flaw. If the endoscope apparatus disclosed in Japanese Patent Application Laid-Open Publication No. 2009-199089 is employed, it is possible to accurately measure the dimension of the flaw and the like and surely determine whether the inspection object is non-defective or defective.

SUMMARY OF THE INVENTION

An endoscope apparatus according to one aspect of the present invention includes: a reference image generating section that generates one or a plurality of reference images to be used for determining whether an inspection object is non-defective or defective; and a mixer that outputs the reference image in a superimposed manner on a moving image of the inspection object whose image is being picked up, in a predetermined inspection mode.

Furthermore, an inspection method using an endoscope according to one aspect of the present invention, includes: a process in which a distance between an inspection object and a distal end portion of an insertion portion is set to a prescribed distance; a process in which a reference image to be used for determining whether the inspection object is non-defective or defective is generated; and a process in which the reference image is superimposed on a moving image of the inspection object whose image is being picked up, in a predetermined inspection mode.

BRIEF DESCRIPTION OF THE DRAWINGS

FIG. 6 is a flowchart showing reference image display processing according to the second embodiment.

DETAILED DESCRIPTION OF THE PREFERRED EMBODIMENTS

Hereinafter, embodiments of the present invention will be described with reference to drawings.

(First Embodiment)

Figure 1:
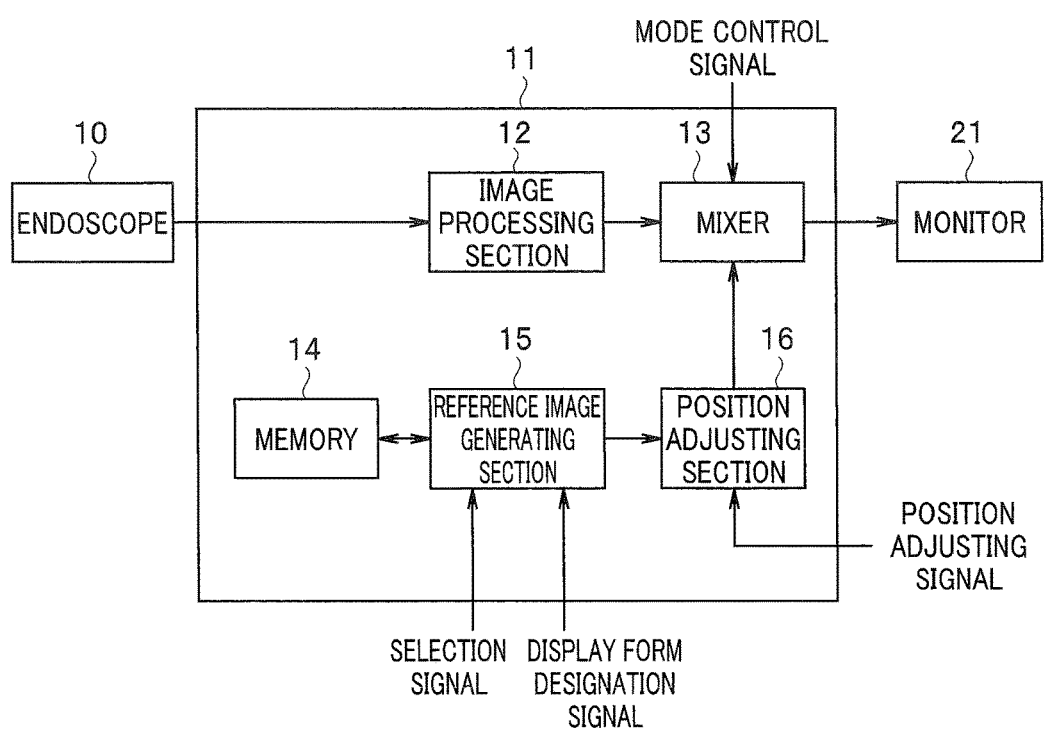
FIG. 1 is a block diagram illustrating an endoscope apparatus according to a first embodiment of the present invention.

FIG. 1 is a block diagram showing an endoscope apparatus according to the first embodiment of the present invention.

In FIG. 1, an endoscope 10 is a rigid endoscope, for example, and includes on a distal end side thereof an elongated insertion portion, not shown. For example, the endoscope 10 may be configured to include an image pickup device such as CCD, CMOS sensor, or the like at the distal end portion of the insertion portion, or may be configured such that a camera, which incorporates an image pickup device, is attached to an eye piece portion located on the proximal end side of the insertion portion. The endoscope 10 converts an optical image from an inspection object into an image signal by using the image pickup device, and outputs an endoscopic image as a moving image or a still image.

The endoscopic image from the endoscope 10 is supplied to a processor unit 11. An image processing section 12 in the processor unit 11 receives the endoscopic image from the endoscope 10, performs predetermined image signal processing on the endoscopic image, and outputs a video signal. For example, the image processing section 12 performs γ-correction processing, white balance adjustment processing, and the like on the endoscopic image, and thereafter outputs the endoscopic image subjected to the processing to a mixer 13.

In the present embodiment, a reference image generating section 15 is provided. The reference image generating section 15 is configured to be able to generate a reference image for determining whether an inspection object is non-defective or defective when performing inspection of the inspection object using the endoscope 10. A memory 14 stores one or more pieces of reference image information. Specified reference image information may be stored in advance in the memory 14 at the time of factory shipment, or reference image information may be generated and stored in the memory 14 by user operation.

The reference image generating section 15 is configured to receive an operation signal based on an input operation performed by the user on an input device, not shown, and cause the memory 14 to store reference image information corresponding to the input operation. In addition, the reference image generating section 15 may import reference image information recorded in a transportable recording medium, through an external memory device, not shown, to cause the memory 14 to record the reference image information.

As the reference image information, for example, information on a cross-shaped image including scale marks formed at predetermined intervals, information on a mesh image including lines or grid arranged at predetermined intervals, character information, shape information of a non-defective inspection object, shape information of a defective inspection object, or the like can be considered. Note that there is a case where accuracy of the reference image information would be sufficient if the reference image enables a user to visually determine whether the inspection object is non-defective or defective when the reference image is displayed on a display screen 21*a* of a monitor 21, to be described later.

The reference image information stored in the memory 14 may include information on color and line width, information on transmissivity (transparency), and the like. In addition, the reference image information may be vector data or raster data. Or, the reference image information may be a figure created with common graphic software, etc., a figure created with handwriting input software, or the like.

The reference image generating section 15 reads out the reference image information from the memory 14, to generate display data (bit map data) of the reference image. For example, the reference image generating section 15 may read out the reference image information designated by a selection signal based on the input operation performed by the user on the input device, not shown.

In the present embodiment, the reference image generating section 15 is configured to output a reference image having a prescribed size such that the reference image is displayed in a predetermined size when the reference image is displayed on the monitor 21. In addition, the reference image generating section 15 sets the color, line width, and transmissivity of the reference image according to the information on the color and line width, and the information on the transmissivity, which are included in the reference image information. Furthermore, the reference image generating section 15 may change the color, line width, and transmissivity of the reference image to the designated color, line width, and transmissivity, based on a display form designation signal corresponding to user operation or information determined in advance.

The reference image generating section 15 outputs the display data of the generated reference image to a position adjusting section 16. The position adjusting section 16 receives a position adjusting signal based on the input operation performed by the user on the input device, not shown, to correct the display data such that the image position of the reference image on the display screen of the monitor 21 is located at the position corresponding to the position adjusting signal. The display data from the position adjusting section 16 is transmitted to the mixer 13. Note that the position adjusting processing to be performed by the position adjusting section 16 is not indispensable. The position adjusting section 16 can be omitted.

The above-described reference image generating processing may be carried out by recording a program for carrying out the processing in a computer-readable recording medium and causing a computer system to read and execute the program recorded in the recording medium. The "computer system" referred to here may include an operating system (OS) and hardware such as peripheral devices.

The mixer 13 is configured to synthesize the endoscopic image received from the image processing section 12 with the reference image received from the position adjusting section 16, to output the synthesized image to the monitor 21.

The mixer 13 receives a mode control signal based on the user operation performed on the input device, not shown. The mode control signal indicates whether or not to synthesize the endoscopic image with the reference image. The mixer 13 is controlled by the mode control signal, to output only the endoscopic image or the synthesized image obtained by synthesizing the endoscopic image with the reference image to the monitor 21.

The monitor 21 receives the video signal from the mixer 13, to display the image based on the inputted video signal on the display screen. Thus, on the display screen of the monitor 21, the endoscopic image is displayed independently or the endoscopic image on which the reference image is superimposed is displayed.

Figure 2:
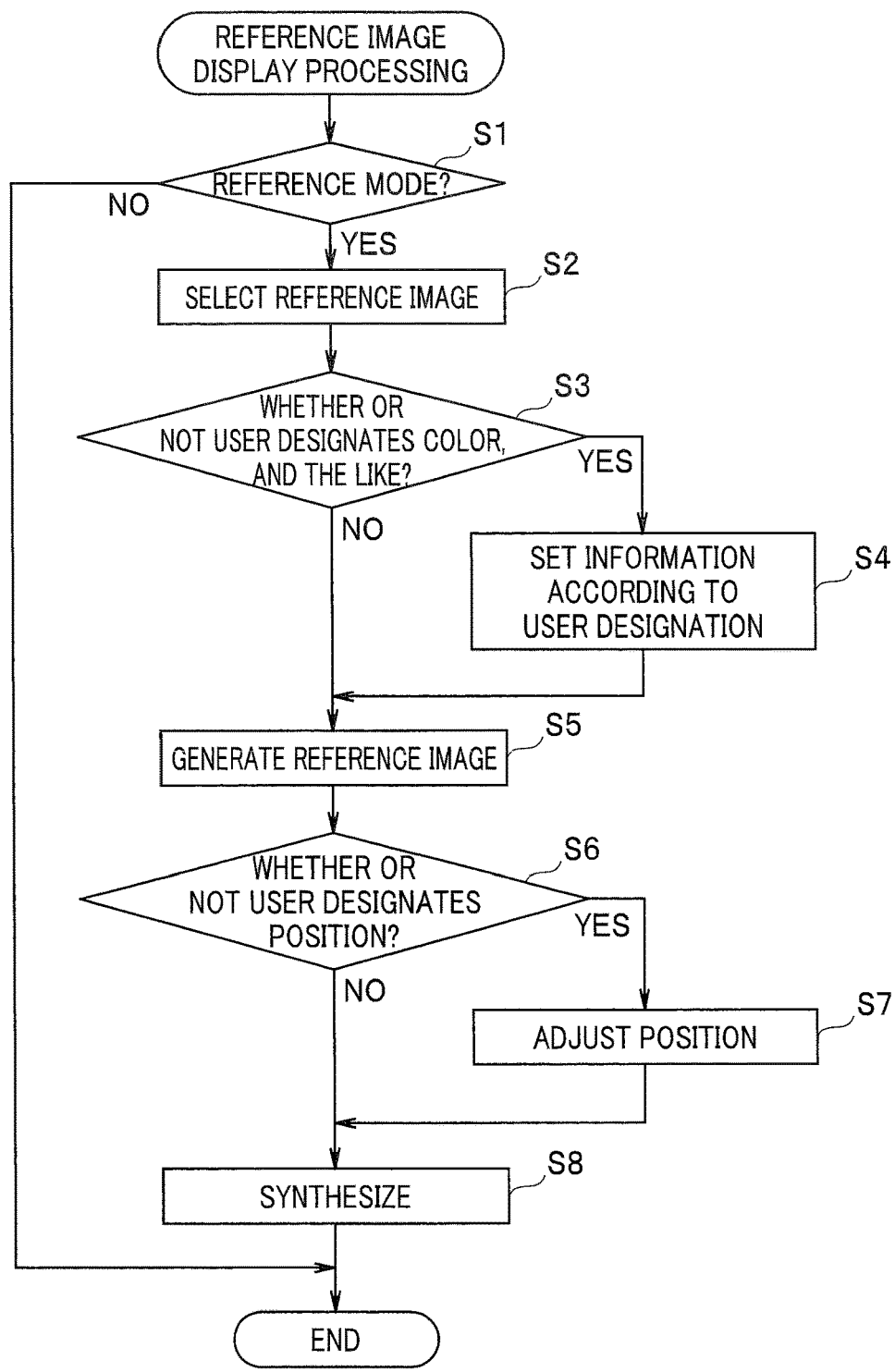
FIG. 2 is a flowchart showing display processing of a reference image.
Figure 3A:
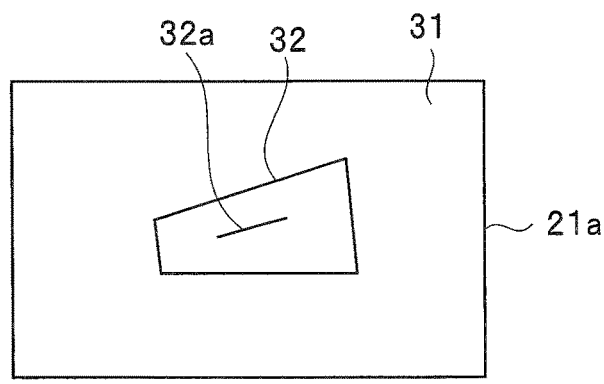
FIGS. 3A to 3C are illustration diagrams for illustrating display of the reference image.
Figure 3B:
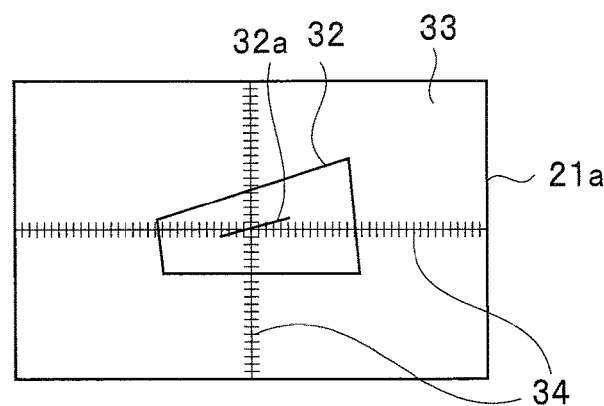
Figure 3C:
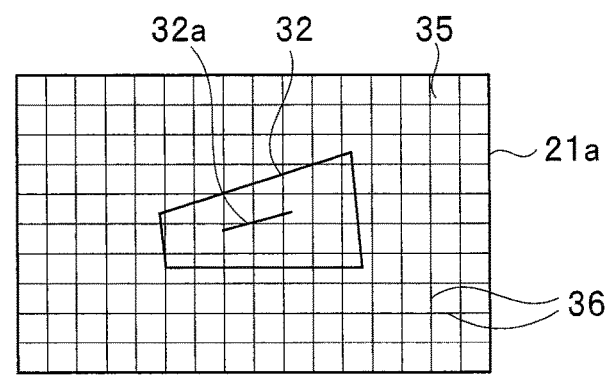
Figure 4A:
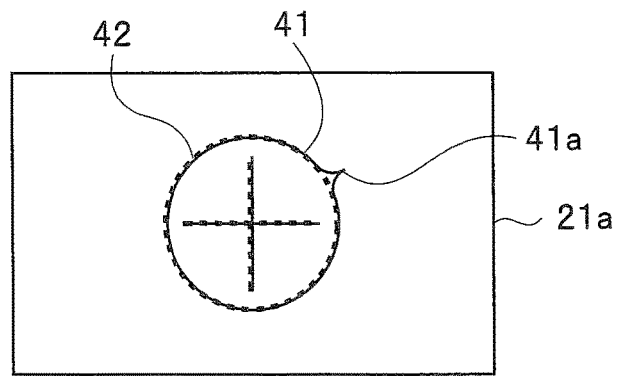
FIGS. 4A to 4C are illustration diagrams for illustrating other examples of the reference image.
Figure 4B:
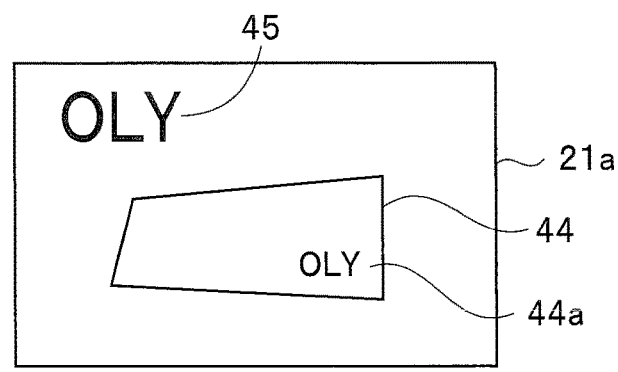
Figure 4C:
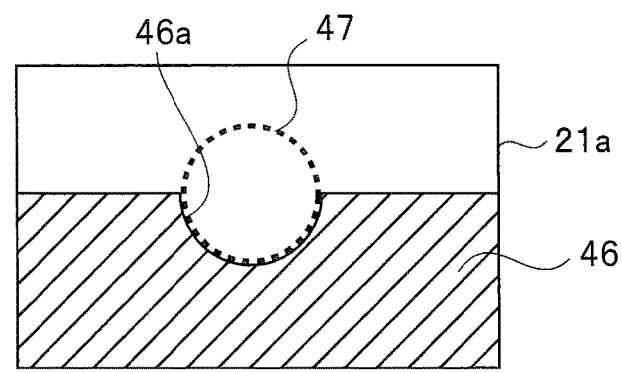

Next, the operation of the embodiment thus configured will be described with reference to FIG. 2 and FIGS. 3A to 3C. FIG. 2 is a flowchart illustrating the display processing of the reference image, and FIGS. 3A to 3C are illustration diagrams for illustrating the display of the reference image. In addition, FIGS. 4A to 4C are illustration diagrams for illustrating other examples of the reference image.

The endoscope 10 is inserted into an inspection hole using a jig, to perform inspection of an inspection object. The endoscopic image from the endoscope 10 is subjected to the image processing by the image processing section 12, and then supplied to the monitor 21 through the mixer 13. The distance between the inspection object and the distal end portion of the insertion portion of the endoscope 10 is set to a prescribed distance, and the endoscopic image of the inspection object obtained by the endoscope 10 is displayed in a prescribed size on the display screen of the monitor 21.

In step S1 in FIG. 2, determination is made on whether or not a reference mode in which the reference image is displayed is designated by the mode control signal, among a plurality of inspection modes. When the reference mode is not designated, the display processing of the reference image is terminated. In this case, the mixer 13 outputs only the endoscopic image received from the image processing section 12 to the monitor 21.

FIG. 3A illustrates the endoscopic image (inspection image) 31 displayed on the display screen 21a of the monitor 21 in the above-described case. An inspection object 32 is displayed in the inspection image 31 at substantially the center position. The inspection object 32 has a flaw 32a.

When the reference mode is designated by the user, a reference image generating section 15 selects a reference image in step S2. For example, the reference image generating section 15 displays on a display section, not shown, a menu for the user to select a reference image, and reads out from the memory 14 the reference image information corresponding to the selection operation by the user. Note that the reference image generating section 15 may read out prescribed reference image information, which is predetermined in advance, from the memory 14, without making inquiries to the user.

Next, in step S3, the reference image generating section 15 determines whether or not the user designates the color, line width, and transmissivity of the reference image. When the user designates the color and the like, the reference image generating section 15 sets the information on the color and the like for the reference image instead of the existing setting, or newly sets the information on the color and the like (step S4).

Next, the reference image generating section 15 generates the display data of the reference image based on the reference image information and the information on the color, line width, and transmissivity, in step S5. The reference image generating section 15 outputs the generated display data of the reference image to the position adjusting section 16.

Next, in step S6, the position adjusting section 16 determines whether or not the designation operation of the display position of the reference image is performed by the user. When the designation operation of the display position is performed, the position adjusting section 16, based on the user operation, rewrites the display data, to change the display position of the reference image. The display data of the reference image from the position adjusting section 16 is supplied to the mixer 13.

When the reference mode is selected, the mixer 13 generates a synthesized image by superimposing the reference image on the endoscopic image (inspection image). The synthesized image is supplied to the monitor 21, and thereby the reference image is displayed superimposed on the inspection image on the display screen.

Note that, also while the reference image is being displayed, the reference image generating section 15 and the position adjusting section 16 can perform operation based on the user operation, and may accept, during the display of the reference image, the selecting, changing or adding operation, designation operation of the color, etc., the designation operation of the display position of the reference image information, and the like, which are performed by the user.

In addition, if the endoscope apparatus is configured such that the reference mode is designated and prescribed reference image information is selected in the initial state, the synthesized image in which the reference image is superimposed on the inspection image can be displayed on the monitor 21 only by turning on the power source of the apparatus.

FIG. 3B illustrates a display example in the case where the reference mode is designated during the display as shown in FIG. 3A, and shows an example in which a cross-shaped scale image is selected as the reference image. In an inspection image 33 on the display screen 21a of the monitor 21, a scale image 34 is superimposed on the inspection object 32. The scale image 34 includes scale marks displayed at prescribed intervals, for example, 1-mm intervals on the display screen 21a. Through the use of the scale marks, the length of the flaw 32a of the inspection object 32 can be easily recognized in the example in FIG. 3B.

FIG. 3C illustrates another example of the reference image. In the inspection image 35 on the display screen 21a as shown in FIG. 3C, a mesh image 36 is displayed superimposed on the inspection object 32. The mesh image 36 includes vertical lines and horizontal lines arranged vertically and horizontally at prescribed intervals, for example, 5-mm intervals on the display screen 21a. Through the use of the mesh image 36, the length of the flaw 32a of the inspection object 32 can be easily recognized in the example in FIG. 3C.

FIGS. 4A to 4C show other reference images. FIG. 4A shows a screw-shaped reference image including a shape of non-defective inspection object. The user designates a type, size, model number, and the like of the screw, and thereby enables the reference image generating section 15 to read out the reference image information of the corresponding screw from the memory 14 and generate a reference image. In the example in FIG. 4A, an inspection object 41 is shown with thin lines, and a reference image 42 is shown with thick dashed lines. A burr 41a is generated at a part of the periphery of the inspection object 41. In the example in FIG. 4A, the image of the inspection object 41 and the reference image 42 are displayed in a superimposed manner, thereby enables the user to easily determine that the burr 41a is generated at the inspection object 41a from the display on the display screen 21a.

FIG. 4B shows an example in which characters 45 are displayed as the reference image. For example, in the case where characters 44a are written in an inspection object 44, the user can easily determine whether or not the characters 44a in the inspection object 44 are correctly written based on the characters 45 as the reference image.

FIG. 4C shows an example in which the image of a part of the outline of the inspection object is displayed as the reference image. The reference image (bold dashed line) in FIG. 4C is a circular image 47, and can be used in the case where a part of the outline of the inspection object is arc-shaped, for example. Depending on whether the circular image 47 as the reference image can be fitted in a recessed portion 46a of an inspection object 46 shown by the diagonal line portion, the user can easily determine whether or not the recessed portion 46a of the inspection object 46 is properly formed.

Note that, in the above-described description, description has been made supposing that the reference image generating section 15 selects only one piece of reference image information. However, the reference image generating section 15 can select a plurality of pieces of reference image information simultaneously, and display the plurality of pieces of reference image information in a synthesized manner. For example, the cross-shaped cursor and the image of the shape of the non-defective inspection object can be displayed superimposed on the inspection image.

Thus, in the present embodiment, the reference image for inspection can be displayed superimposed on the endoscopic image, which enables the user to easily determine whether the inspection object is non-defective or defective by comparing the image of the inspection object with the reference image. In addition, the reference image can be switched not only by turning on or off the display of the reference image but also by selecting the reference image information stored in the memory. As a result, a reference image tailored to the inspection object can be easily displayed. Furthermore, the color, line width, transmissivity, display position and the like of the reference image can be freely changed, to thereby further facilitate the user's determination on whether the inspection object is non-defective or defective.

(Second Embodiment)

Figure 5:
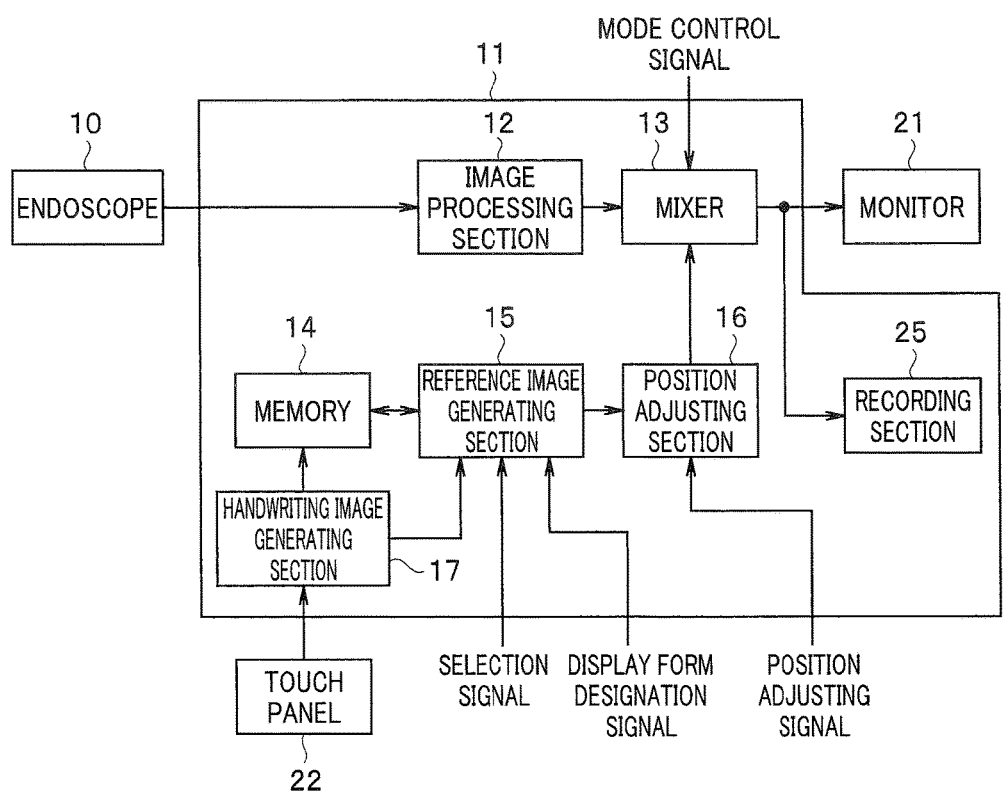
FIG. 5 is a block diagram showing a second embodiment of the present invention.

FIG. 5 is a block diagram showing the second embodiment of the present invention. Constituent elements in FIG. 5 which are the same as those in FIG. 1 are attached with the same reference numerals and descriptions thereof will be omitted. The present embodiment is different from the first embodiment in that a handwriting image generating section 17, a touch panel 22, and a recording section 25 are additionally provided.

The touch panel 22 is disposed on the display screen 21a of the monitor 21. The touch panel 22 is capable of generating an operation signal corresponding to the position on the display screen 21a which is pointed by the user with a finger, and the like. The operation signal is supplied to the handwriting image generating section 17. When the user touches or slides the display screen 21a, the handwriting image generating section 17 is capable of detecting a touch position by the user, sliding operation, the positions sequentially reached by the sliding operation, the sliding direction, a time period during which the user touches the display screen, various kinds of operations such as operation for closing and then spreading the fingers (pinch operation), and the like.

Based on the detection, for example, the handwriting image generating section 17 is capable of acquiring the coordinates of the slide locus drawn by the sliding operation performed by the user on the touch panel 22, detecting a line formed by the sliding operation, sending, as the reference image information, the figure which is the detection result to the memory 14, to cause the memory 14 to store the figure, and outputting the figure to the reference image generating section 15. Note that the handwriting image generating section 17 may be configured to be able to designate the color, thickness (line width), transmissivity, and the like, of the line and perform editing operation such as designation for filling a closed region, deletion of the detected line, etc., in response to the various kinds of operation on the touch panel 22.

When a handwriting registration mode is designated by the user operation on the input device, not shown, the reference image generating section 15 is capable of outputting the image of the detected figure received from the handwriting image generating section 17. The image of the detected figure is supplied to the monitor 21 through the position adjusting section 16 and the mixer 13, and the operation performed by the user on the touch panel 22 is reflected on the display screen 21a of the monitor 21 so that the state of generation of the handwriting figure can be confirmed. Furthermore, the reference image generating section 15 is also capable of synthesizing another piece of reference image information read out from the memory 14 with the image of the detected figure received from the handwriting image generating section 17, to output the result of the synthesizing.

A recording section 25 receives a synthesized image from the mixer 13. The recording section 25 is capable of recording the image at a timing designated by the user.

Next, the operation in the embodiment thus configured will be described with reference to FIGS. 6 to 8. FIG. 6 is a flowchart showing the reference image display processing in the second embodiment. In FIG. 6, the processing steps same as those in FIG. 2 are attached with the same reference numerals and descriptions thereof will be omitted.

Also in the present embodiment, the same inspection as that in the first embodiment is performed. A reference image with handwriting can be displayed also in the first embodiment. However, the present embodiment is different from the first embodiment in that a handwriting reference image can be generated.

Figure 7A:
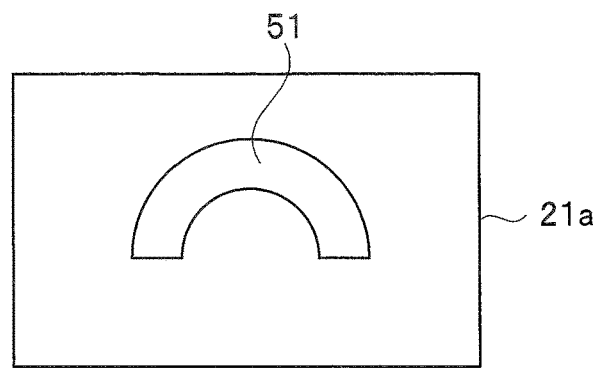
FIGS. 7A and 7B are illustration diagrams for illustrating display of the reference image according to the second embodiment.
Figure 7B:
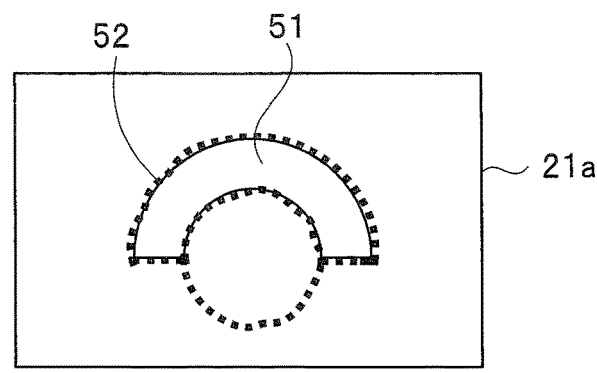
Figure 8:
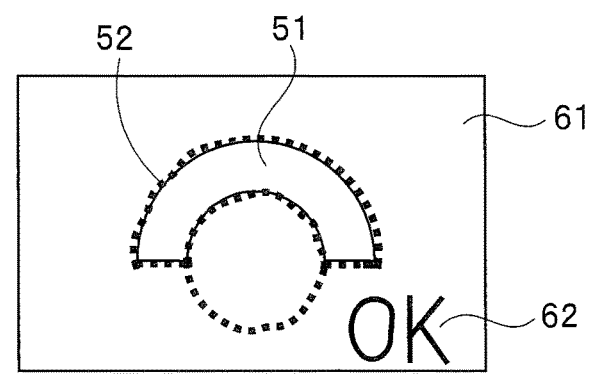
FIG. 8 is an illustration diagram showing one example of a recorded image.

FIGS. 7A and 7B are illustration diagrams for illustrating display of the reference images in the present embodiment. FIG. 7A shows a display in the state where only the endoscopic image from the image processing section 12 is outputted by the mixer 13 to the monitor 21. As shown in FIG. 7A, an inspection object 51 is displayed on the display screen 21a.

When the reference image information corresponding to the inspection object 51 is not included in the memory 14, the user generates a reference image with handwriting input. In step S11 in FIG. 6, determination is made on whether or not the handwriting registration mode is designated. When the user designates the handwriting registration mode, the processing procedure moves to step S12, and handwriting figure is generated. When the user writes a figure by operating the touch panel 22 on the display screen 21a of the monitor 21, the handwriting image generating section 17 detects the figure by using the coordinates of the locus drawn by the sliding operation by the user, to sequentially output the detection result to the reference image generating section 15.

In the handwriting registration mode, the reference image generating section 15 outputs the image of the figure created by the handwriting image generating section 17. This allows the figure which is being created by the user to be displayed on the display screen 21a of the monitor 21.

For example, the user determines that the inspection object 51 displayed on the display screen 21a is non-defective and traces the outline of the inspection object 51 with a finger and the like on the touch panel 22, to thereby generate a reference image corresponding to the inspection object 51 with handwriting input.

FIG. 7B illustrates a reference image 52 thus generated, with the thick dashed lines. The figure detected by the handwriting image generating section 17 is sent to the memory 14 as the reference image information and recorded in the memory 14.

Note that, in the handwriting registration mode, the output from the handwriting image generating section 17 is displayed, as the reference image, so as to be superimposed on the inspection image. Therefore, it is not necessary to store the handwriting image as the reference image information in the memory 14. In addition, the reference image generating section 15 may output only the image detected by the handwriting image generating section 17 without reading out the reference image information from the memory 14.

Note that, even while the handwriting registration mode is selected, the reference image generating section 15 and the position adjusting section 16 can perform operation based on user operation, and may accept, during the display of the reference image generated with handwriting, the operations performed by the user such as selecting, changing, or adding operation, designation operation of the color, etc., the designation operation of the display position, and the like of the reference image information.

In addition, in the present embodiment, when recording operation is performed by the user, recording processing is performed by the recording section 25 in step S13. FIG. 8 is an illustration diagram for illustrating one example of a recorded image 61 in the recording processing. The recorded image 61 shown in FIG. 8 includes the inspection object 51, the reference image 52, and an image 62 indicating the inspection result. The image 62 is generated by the handwriting image generating section 17 based on the user operation. Note that, the reference image generating section 15 may delete the reference image 52 and output only the image 62, and may record, in the recording section 25, a recorded image including only the inspection object 51 and the image 62 indicating the result of non-defective/defective determination, or may record the image in which only the reference image 52 is superimposed on the inspection object 51.

Thus, also the present embodiment is capable of providing the same effects as those in the first embodiment. Furthermore, in the present embodiment, the reference image can be generated with handwriting. Even in the case where the reference image information corresponding to the inspection object is not stored in the memory, reference image information can be easily generated with handwriting and the generated reference image information can be displayed. Furthermore, the inspection image is kept being displayed during the generation of the reference image, and the reference image information to be used for non-defective/defective determination can be generated by the extremely simple operation of tracing the outline of the inspection object, which enables the inspection of non-defective or defective object to be simplified. In addition, the handwriting image generated by the handwriting image generating section 17 can be included in the recorded image, and the user is capable of recording the inspection result with simple operation.

In addition, in the above-described respective embodiments, description has been made supposing that the menu is displayed so that the user can select the reference image information. The menu may be hierarchized according to the inspection contents, and only the reference image information corresponding to the inspection may be allowed to be selected by the user.

The present invention is not limited to the above-described embodiments as they are, but can be embodied by modifying constituent elements in the practical stage within a range without departing from the gist of the invention. Furthermore, various inventions can be formed by appropriately combining the plurality of constituent elements disclosed in each of the embodiments. For example, among all of the constituent elements shown in the embodiments, some constituent elements may be removed. Furthermore, the constituent elements from different embodiments may be appropriately combined.

In addition, among the techniques described above, many of the controls and functions described mainly in the flowcharts can be set by a program, and the above-described controls and functions can be executed by reading and executing the program by a computer. The entirety or a part of such a program can be recorded or stored as a computer program product in a transportable medium such as a flexible disk, CD-ROM and a nonvolatile memory, or a storage medium such as a hard disk and a volatile memory, and can be distributed or provided at the time of product shipment or through a transportable medium or telecommunications line. A user can easily realize the present embodiments by downloading the program through a communication network to install the program into a computer, or by installing the program from a recording medium into a computer.

Note that, even if description is made by using the expressions "first", "next" and the like with regard to the operation flow, for convenience sake, it does not mean that processing steps have to be executed in this order. In addition, needless to say, each of the steps constituting the operation flow may be appropriately omitted regarding the part which does not affect the essential part of the invention.

What is claimed is:

1. An apparatus comprising:
a processor comprising hardware, wherein the processor is configured to:
generate a moving image of an inspection object based on signals acquired from an image sensor of an endoscope that converts an object image of the inspection object to the signals;
control a display to display the moving image;
generate a user-generated reference image for determining whether the inspection object is non-defective or defective, wherein the user-generated reference image is generated based on a first handwriting operation of a user received by an input device as the moving image is displayed by the display;
control the display to display the user-generated reference image superimposed on the moving image;
generate a user-generated inspection result image based on a second handwriting operation of the user received by the input device, wherein the user-generated inspection result image indicates an inspection result of whether the inspection object is non-defective or defective;
control the display to display an inspected image comprising the user-generated reference image and the user-generated inspection image superimposed on the moving image; and
control a storage device to store the inspected image.

2. The apparatus according to claim 1,
wherein the processor is configured to:
generate one or more predetermined reference images based on a corresponding one or more predetermined reference image information stored in advance in the storage device; and
control the display to display the one or more predetermined reference images superimposed on the moving image.

3. The apparatus according to claim 2,
wherein the processor is configured to:
selectively read out at least one of the one or more predetermined reference image information based on a selection by the user; and
generate the one or more predetermined reference images based on the at least one of the one or more predetermined reference image information selectively read out.

4. The apparatus according to claim 2,
wherein the processor is configured to cause the storage device to store information on the user-generated reference image as the one or more predetermined reference image information stored in advance which can be selectively read out in the future to generate the one or more predetermined reference images.

5. The apparatus according to claim 2,
wherein the processor is configured to adjust a display position where the one or more predetermined reference images are superimposed on the moving image.

6. The apparatus according to claim 2,
wherein the processor is configured to control the storage device to store an image in which the one more predetermined reference images are superimposed on the moving image.

7. The apparatus according to claim 2,
wherein each of the one or more predetermined reference images is a shape image of the inspection object in a non-defective state or a shape image of the inspection objection in a defective state.

8. The apparatus according to claim 2,
wherein at least one of the one or more predetermined reference images is an image of characters.

9. The apparatus according to claim 2,
wherein at least one of the one or more predetermined reference images is an image of a part of an outline of the inspection object.

10. The apparatus according to claim 2,
wherein the processor is configured to:
  select a plurality of the predetermined reference image information stored in advance in the storage device; and
  control the display to display a corresponding plurality of the predetermined reference images based on the plurality of the predetermined reference image information selected.

11. The apparatus according to claim 1, further comprising:
the display; and
a touch panel disposed on a display screen of the display section, wherein the touch panel is the input device configured to receive the first handwriting operation and the second handwriting operation of the user.

12. The apparatus according to claim 1,
wherein the processor is configured to receive the second handwriting operation of the user during control of the display to display the user-generated reference image superimposed on the moving image.

13. A method comprising:
setting a distance between an inspection object and an image sensor arranged at a distal end portion of an insertion portion of an endoscope a prescribed distance;
generating one or more a reference images to be used for determining whether the inspection object is non-defective or defective,
  wherein one of the one or more reference images is an image of a part of an outline of the inspection object,
generating a moving image of the inspection object based on signals acquired from the image sensor that converts an object image of the inspection object to the signals; and
superimposing the one or more reference images on the moving image,
  wherein the superimposing comprises superimposing the image of the part of the outline of the inspection object on a portion of the moving image showing a recessed portion of the inspection object.

14. The method according to claim 13,
wherein the generating the one or more reference images comprises
  generating a user-generated reference image, as one of the one or more reference images, based on a handwriting operation of a user received by an input device.

15. The method according to claim 13,
wherein another of the one or more reference images is a scale image,
  wherein the method further comprises adjusting a display position where the scale image is superimposed on the moving image.

16. The method according to claim 13, further comprising:
  wherein another of the one or more reference images is an image of a shape of a non-defective inspection object or an image of a shape of a defective inspection object, and
  wherein the method further comprises adjusting a display position where the image of the shape of the non-defective inspection object or a display position of the image of the shape of the defective inspection object is superimposed on the moving image.

17. The method according to claim 14,
wherein the generating the user-generated reference image comprises generating the user-generated reference image based on the handwriting operation of the user in a state where the moving image of the inspection object is displayed.

18. A method comprising:
generating a moving image of an inspection object based on signals acquired from an image sensor of an endoscope that converts an object image of the inspection object to the signals;
controlling a display to display the moving image;
generating a user-generated reference image for determining whether the inspection object is non-defective or defective, wherein the user-generated reference image is generated based on a first handwriting operation of a user received by an input device as the moving image is displayed by the display;
controlling the display to display the user-generated reference image superimposed on the moving image;
generating a user-generated inspection result image based on a second handwriting operation of the user received by the input device, wherein the user-generated inspection result image indicates an inspection result of whether the inspection object is non-defective or defective;
controlling the display to display an inspected image comprising the user-generated reference image and the user-generated inspection image superimposed on the moving image; and
controlling a storage device to store the inspected image.

19. A non-transitory computer-readable recording medium storing instructions that cause a computer to at least perform:
generating a moving image of an inspection object based on signals acquired from an image sensor of an endoscope that converts an object image of the inspection object to the signals;
controlling a display to display the moving image;
generating a user-generated reference image for determining whether the inspection object is non-defective or defective, wherein the user-generated reference image is generated based on a first handwriting operation of a user received by an input device as the moving image is displayed by the display;
controlling the display to display the user-generated reference image superimposed on the moving image;
generating a user-generated inspection result image based on a second handwriting operation of the user received by the input device, wherein the user-generated inspection result image indicates an inspection result of whether the inspection object is non-defective or defective;

controlling the display to display an inspected image comprising the user-generated reference image and the user-generated inspection image superimposed on the moving image;

and controlling a storage device to store the inspected image.

* * * * *